US009035061B2

(12) United States Patent
Colson

(10) Patent No.: US 9,035,061 B2
(45) Date of Patent: May 19, 2015

(54) PROCESS FOR PREPARING A BIPHENYL-2-YLCARBAMIC ACID

(71) Applicant: Pierre-Jean Colson, San Francisco, CA (US)

(72) Inventor: Pierre-Jean Colson, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 14/090,211

(22) Filed: Nov. 26, 2013

(65) Prior Publication Data

US 2014/0121378 A1  May 1, 2014

Related U.S. Application Data

(62) Division of application No. 13/173,274, filed on Jun. 30, 2011, now Pat. No. 8,754,225.

(60) Provisional application No. 61/363,725, filed on Jul. 13, 2010.

(51) Int. Cl.
*C07D 211/46* (2006.01)
*C07D 401/12* (2006.01)

(52) U.S. Cl.
CPC ............ *C07D 401/12* (2013.01); *C07D 211/46* (2013.01)

(58) Field of Classification Search
CPC .......................... C07D 211/40; C07D 211/46
USPC .......................................... 546/216, 188, 222
See application file for complete search history.

(56) References Cited

U.S. PATENT DOCUMENTS

| 7,141,671 | B2 * | 11/2006 | Mammen et al. ............. 546/224 |
| 7,288,657 | B2 | 10/2007 | Mammen et al. |
| 7,345,060 | B2 | 3/2008 | Mammen et al. |
| 7,659,403 | B2 | 2/2010 | Mu et al. |
| 7,700,777 | B2 | 4/2010 | Axt et al. |
| 8,541,451 | B2 | 9/2013 | Woollam |

OTHER PUBLICATIONS

Mammen et al. "Preparation of biphenyl . . . " CA141:225161 (2004).*
Aul et al. "A green alternative . . . " Manufacturing Chemist , May, p. 33-34 (2007).*
Solvehts Wikipedia p. 1-10 (2011).*
Walton et al. "Solvents and solvent effects . . . " appendix (2011).*
Armarego, "Purificatio of laboratory chemicals", p. 11 (1996).
International Search Report for PCT/US2011/042530 dated Dec. 14, 2011.
Joullie et al., "Evolution of amide . . . "ARKIVOC viii p. 189-250 (2010).
Martin et al., "Total Syntheses of the Amaryllidaceae Alkaloids Haemanthidine and Pretazettine", Journal of Organic Chemistry, 52, pp. 1962-1972 (1987).
Wikipedia, "Azeotropic distillation", p. 1-2 (2013 from Internet).

* cited by examiner

*Primary Examiner* — Celia Chang
(74) *Attorney, Agent, or Firm* — Jeffrey A. Hagenah

(57) ABSTRACT

The invention provides a process of preparing an intermediate useful in the synthesis of biphenyl-2-ylcarbamic acid 1-(2-{[4-(4-carbamoylpiperidin-1-ylmethyl)benzoyl]methylamino}ethyl)piperidin-4-yl ester, and a process of preparing a crystalline freebase of the ester.

4 Claims, No Drawings

PROCESS FOR PREPARING A BIPHENYL-2-YLCARBAMIC ACID

CROSS-REFERENCE TO RELATED APPLICATIONS

This application is a divisional application of U.S. Ser. No. 13/173,274, filed Jun. 30, 2011, which claims the benefit of U.S. Provisional Application No. 61/363,725, filed on Jul. 13, 2010; the entire disclosures of which are incorporated herein by reference.

BACKGROUND OF THE INVENTION

1. Field of the Invention

The present invention relates to a process of preparing biphenyl-2-ylcarbamic acid 1-(2-{[4-(4-carbamoylpiperidin-1-ylmethyl)benzoyl]methylamino}ethyl)piperidin-4-yl ester. The invention further relates to processes of preparing a crystalline freebase of this ester. The invention also relates to a process of preparing an intermediate useful in the synthesis of the ester and the crystalline freebase.

2. State of the Art

U.S. Pat. No. 7,288,657 to Mammen et al. discloses novel biphenyl compounds that are expected to be useful for treating pulmonary disorders such as chronic obstructive pulmonary disease and asthma. In particular, the compound biphenyl-2-ylcarbamic acid 1-(2-{[4-(4-carbamoylpiperidin-1-ylmethyl)benzoyl]methylamino}-ethyl)piperidin-4-yl ester is specifically described in this application as possessing muscarinic receptor antagonist or anticholinergic activity, and is represented by formula I:

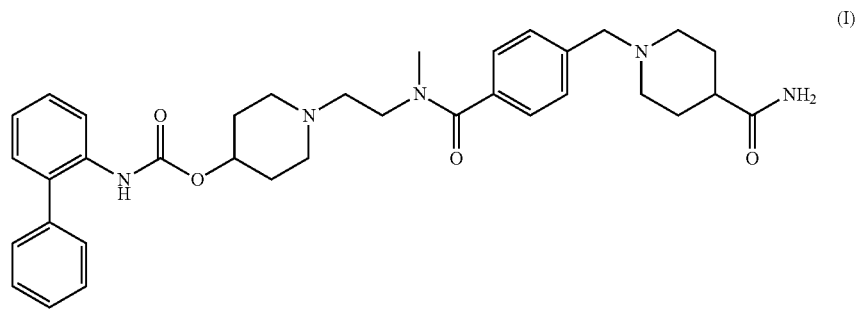 [SMILES: CN(CCN1CCC(OC(=O)Nc2ccccc2-c2ccccc2)CC1)C(=O)c1ccc(CN2CCC(C(N)=O)CC2)cc1]

(I)

The compound of formula I is synthesized from the compound 8, which is described as being prepared from the oxidation of 2-(benzylmethylamino)ethanol to the aldehyde intermediate followed by reductive amination with biphenyl-2-yl-carbamic acid piperidin-4-yl ester and debenzylation:

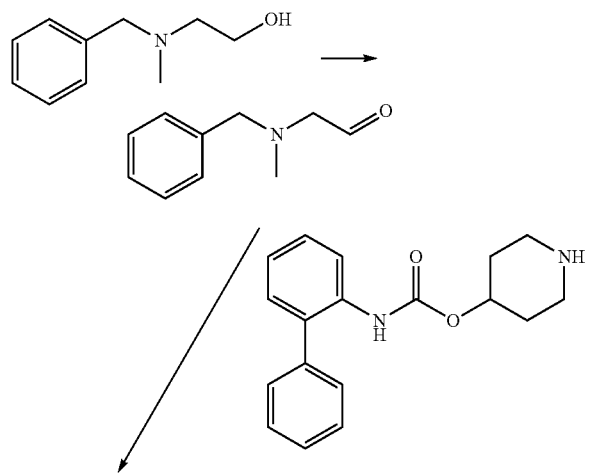

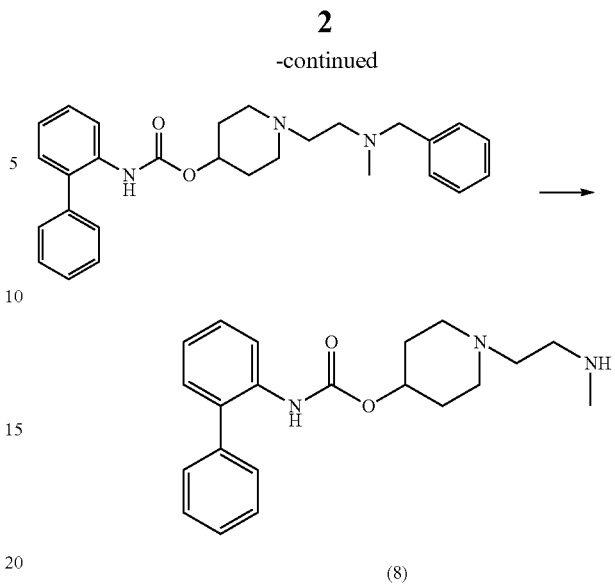

(8)

However, while this procedure performs well on small scale, the aldehyde intermediate is difficult to scale up due to its instability, and low yields were typically observed.

Thus, a need exists for an efficient process of preparing compound 8 as a pure material with high chemical purity and good overall yield, without having to isolate intermediates. This invention addresses those needs.

Therapeutic agents useful for treating pulmonary or respiratory disorders are advantageously administered directly into the respiratory tract by inhalation. In this regard, several types of pharmaceutical inhalation devices have been developed for administering therapeutic agents by inhalation including dry powder inhalers, metered-dose inhalers, and nebulizer inhalers. When preparing pharmaceutical compositions and formulations for use in such devices, it is highly desirable to have a crystalline form of the therapeutic agent that is neither hygroscopic nor deliquescent and which has a relatively high melting point thereby allowing the material to be micronized without significant decomposition.

A crystalline diphosphate of the compound of formula I has been reported in U.S. Pat. No. 7,700,777 to Axt et al, and a crystalline freebase (identified as Form III) is described in U.S. Patent Application Publication No. 2011/0015163 to Woollham. All of the aforementioned disclosures are incorporated herein by reference.

The compound of formula I is described as being prepared by reacting compound 8 with 4-carboxybenzaldehyde to form the aldehyde core 10:

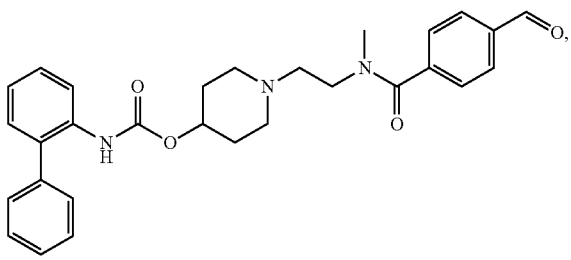
(10)

which is then isolated prior to being combined with isonipi-cotamide in the presence of a reducing agent to form the compound of formula I. The crystalline diphosphate is prepared by contacting the separated and purified compound of formula I with phosphoric acid. The crystalline freebase (Form III) can then be prepared from the crystalline diphosphate.

A need also exists for an efficient process of preparing the crystalline freebase (Form III). It is desirable to develop a process that does not first require preparation of the crystalline diphosphate. This invention addresses those needs.

SUMMARY OF THE INVENTION

The present invention relates to a process for preparing the crystalline freebase (Form III) of biphenyl-2-ylcarbamic acid 1-(2-{[4-(4-carbamoylpiperidin-1-ylmethyl) benzoyl] methylamino}ethyl)piperidin-4-yl ester described in U.S. Patent Application Publication No. 2011/0015163 to Woollham. Form III is characterized by a powder x-ray diffraction pattern comprising diffraction peaks at 2θ values of 6.6±0.1, 13.1±0.1, 18.6±0.1, 19.7±0.1, and 20.2±0.1; and further characterized by having five or more additional diffraction peaks at 2θ values selected from 8.8±0.1, 10.1±0.1, 11.4±0.1, 11.6±0.1, 14.8±0.1, 15.2±0.1, 16.1±0.1, 16.4±0.1, 16.9±0.1, 17.5±0.1, 18.2±0.1, 19.3±0.1, 19.9±0.1, 20.8±0.1, 21.1±0.1, 21.7±0.1, and 22.3±0.1.

One aspect of the invention relates to a process for preparing a crystalline freebase (Form III) of the compound of formula I:

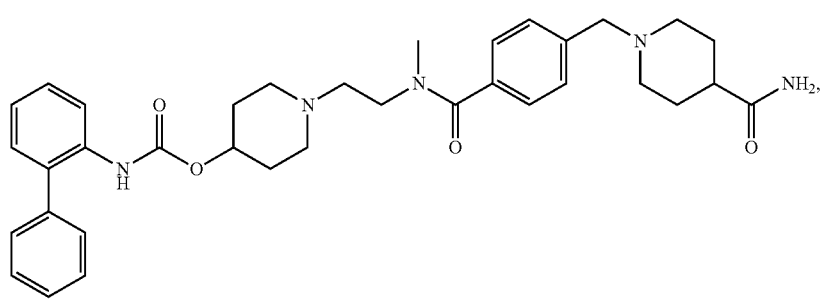
(I)

the process comprising the steps of:

(a) coupling a compound of formula 8:

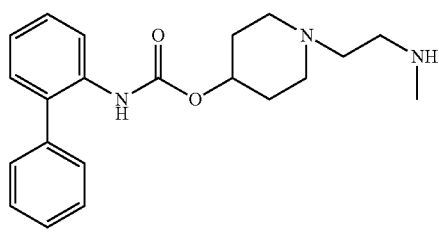
(8)

in the presence of a coupling reagent with a compound of formula 9:

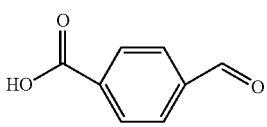
(9)

to yield the compound of formula 10:

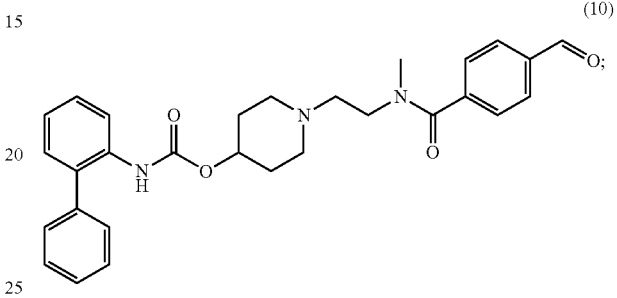
(10)

(b) reductive amination of the compound of formula 10 and a compound of formula 11:

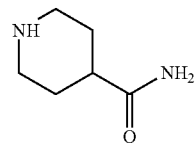
(11)

in the presence of a reducing agent to yield the compound of formula I, wherein azeotropic distillation of water is conducted at an elevated temperature prior to the addition of the reducing agent, and reductive amination is conducted at room temperature;

(c) contacting the product of step (b) with isopropyl acetate, optionally adding a seed crystal of the crystalline freebase (Form III) to form a solid, and isolating the resulting solid; and (d) contacting the product of step (c) with toluene, optionally adding a seed crystal of the crystalline freebase (Form III) to form a solid, and isolating the resulting solid as the crystalline freebase (Form III); wherein step (a) and step (b) are conducted in the same reaction mixture without isolation of the intermediate from step (a).

The present invention further relates to an improved process for preparing an intermediate useful for preparing the crystalline freebase (Form III). Accordingly, another aspect of the invention relates to a process for preparing a compound of formula 8:

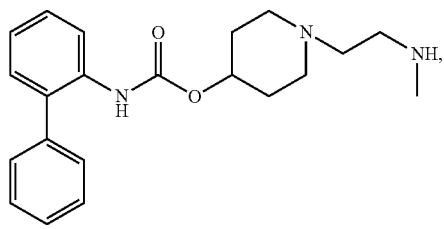
(8)

the process comprising the steps of:
(a) reductive amination of a compound of formula 3:

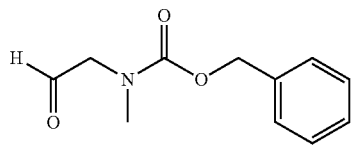
(3)

and a compound of formula 6:

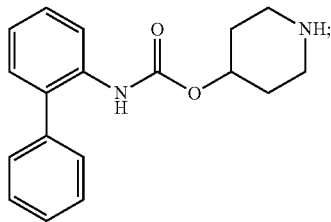
(6)

in the presence of a reducing agent, to yield the compound of formula 7:

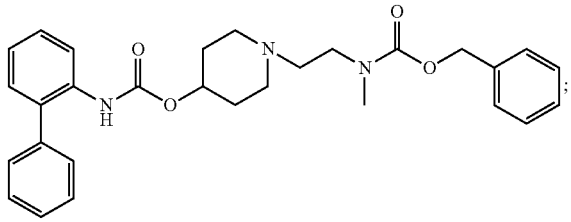
(7)

and
(b) debenzylation of the compound of formula 7 to yield the compound of formula 8; wherein step (a) and step (b) are conducted in the same reaction mixture without isolation of the intermediate from step (a).

The present invention also relates to an improved process for preparing a compound of formula 3:

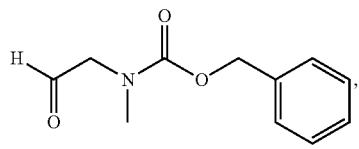
(3)

the process comprising the steps of:
(i) carbobenzyloxy protection of a compound of formula 1:

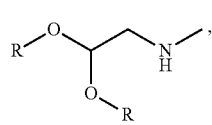
(1)

where each R is independently $C_{1-6}$alkyl or are taken together to form a dioxane or dioxolane, to yield the compound of formula 2:

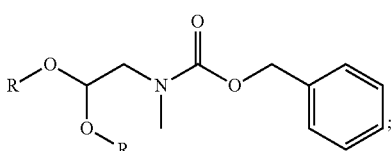
(2)

and
(ii) acetal deprotection of the compound of formula 2 to yield the compound of formula 3. In one embodiment, the compound of formula 3 can be used directly in the synthesis of the compound of formula 8 without first being isolated.

DETAILED DESCRIPTION OF THE INVENTION

The invention relates to novel processes for preparing compounds of formula 8 and a crystalline freebase (Form III) of the compound of formula I. Among other advantages, the process for preparing compounds of formula 8 and the process for preparing the crystalline freebase are conducted in a single reaction vessel without isolation of intermediate reaction products, thereby generating less waste and improving the overall efficiency and yield of the process, compared to other processes.

Definitions

When describing the compounds and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "having the formula" or "having the structure" is not intended to be limiting and is used in the same way that the term "comprising" is commonly used. All other terms used herein are intended to have their ordinary meaning as understood by those of ordinary skill in the art to which they pertain.

Process Conditions

It will be appreciated that while specific process conditions (i.e. crystallization temperatures, times, mole ratios of reactants, solvents, pressures, etc.) are given, other process conditions can also be used unless otherwise stated. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Suitable inert diluents for use in the process of the invention include, by way of illustration and not limitation, organic diluents such as acetic acid, tetrahydrofuran (THF), 2-methyltetrahydrofuran (MeTHF), acetonitrile (MeCN), N,N-dimethylformamide (DMF), N,N-dimethylacetamide, N-methylpyrrolidinone, dimethyl sulfoxide (DMSO), toluene, dichloromethane (DCM), acetone, ethyl acetate, isopropyl acetate, methyl t-butyl ether, chloroform (CHCl$_3$), carbon tetrachloride (CCl$_4$), 1,4-dioxane, methanol, ethanol, propanol, isopropanol, butanol, ethylene glycol, and the like. Aqueous diluents may also be used, and include water as well as basic and acidic aqueous diluents. Combinations of any of the foregoing diluents are also contemplated.

There are numerous bases that are suitable for use in the process of the invention. Exemplary organic bases include, by way of illustration and not limitation: amines including primary alkylamines (e.g., methylamine, ethanolamine, the buffering agent tris, and the like), secondary alkylamines (e.g., dimethylamine, methylethanolamine, N,N-diisopropylethylamine (DIPEA), and the like), tertiary amines (e.g., trimethylamine, triethylamine, triethylenediamine, and the like); ammonia compounds such as ammonium hydroxide and hydrazine; alkali metal hydroxides such as sodium hydroxide, sodium methoxide, potassium hydroxide, potassium t-butoxide, and the like; metal hydrides; and alkali metal carboxylate salts such as sodium acetate and the like). Exemplary inorganic bases, include, by way of illustration and not limitation: alkali metal carbonates such as lithium carbonate, potassium carbonate, cesium carbonate, sodium carbonate, sodium bicarbonate, and the like; other carbonates such as calcium carbonate and the like; and alkali metal phosphates such as potassium phosphate and the like).

All reactions are typically conducted at a temperature within the range of about −78° C. to about 110° C., for example at room temperature. In some instances, reactions were conducted at room temperature and no actual temperature measurement was taken. It is understood that room temperature can be taken to mean a temperature within the range commonly associated with the ambient temperature in a laboratory environment, and will typically be in the range of about 25° C. to about 30° C. In other instances, reactions were conducted at room temperature and the temperature was actually measured and recorded. Reactions may be monitored by use of thin layer chromatography (TLC), high performance liquid chromatography (HPLC), and/or LCMS until completion. Reactions may be complete in minutes, may take hours, typically from 1-2 hours and up to 48 hours, or days, such as up to 3-4 days.

Upon completion of the process, the resulting product may be further treated in order to obtain the desired product. For example, the product may be subjected to one or more of the following procedures: concentrating or partitioning (for example, between EtOAc and water or between 5% THF in EtOAc and 1M phosphoric acid); extraction (for example, with EtOAc, CHCl$_3$, DCM, HCl); washing (for example, with ethanol, heptanes, saturated aqueous NaCl, saturated NaHCO$_3$, Na$_2$CO$_3$ (5%), CHCl$_3$ or 1M NaOH); distillation; drying (for example, over MgSO$_4$, over Na$_2$SO$_4$, under nitrogen, or under reduced pressure); precipitation; filtration; crystallizing (for example, from ethanol, heptanes or isopropyl acetate); and/or being concentrated (for example, in vacuo). More specifically, upon completion of the crystallization process, the crystalline compound can be isolated from the reaction mixture by any conventional means such as precipitation, concentration, centrifugation, drying (for example, at room temperature), and the like.

Compound of Formula 8

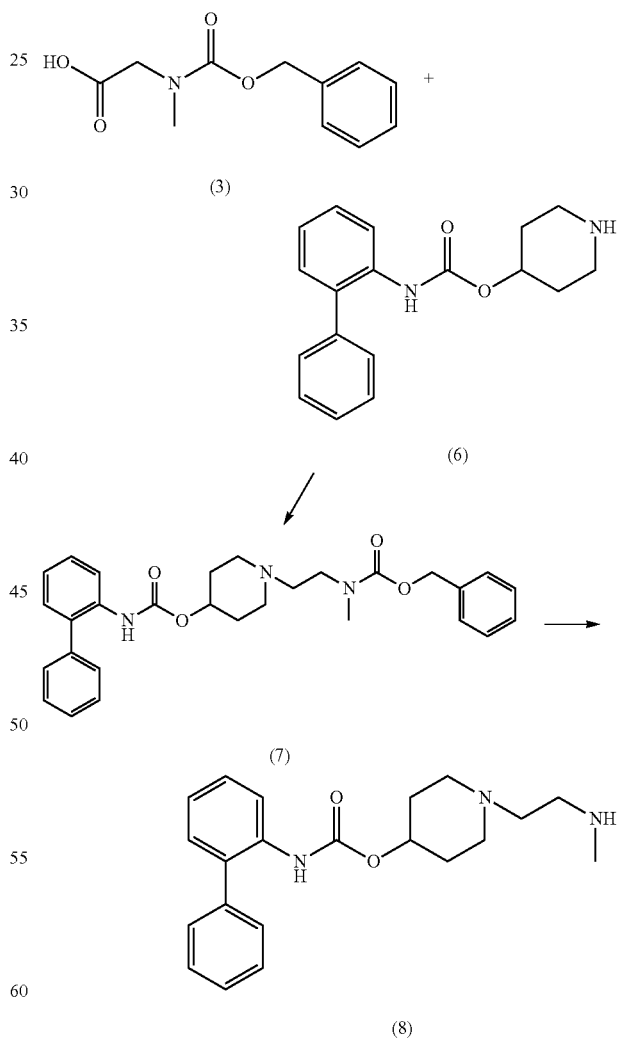

The process for preparing the compound of formula 8 is conducted in two steps, and is conducted in a single reaction vessel without isolation of intermediate reaction products. Generally, for a multi-step process that is conducted in a single reaction vessel, the inert diluent is selected so as to be compatible with the materials used in each step. In one embodiment, the inert diluent is the same in each of the two steps used for preparing the compound of formula 8; and in a particular embodiment, the inert diluent is methyltetrahydrofuran.

The first step of the process is a reductive amination reaction that forms compound 7. This step involves combining about one equivalent of compound 6 with about one equivalent of compound 3 and one or more equivalents of a reducing agent.

Typically, the reducing agent is added to a mixture of compound 6 and compound 3 in an inert diluent such as methyltetrahydrofuran. In one embodiment, about 1.5 to 2.5 equivalents of the reducing agent are used based on the amount of compound 6 and the amount of compound 3; and in another embodiment, about 2.0 equivalents are used.

Suitable reducing agents include metal hydride reagents and borane reducing agents. Exemplary metal hydride reagents include sodium triacetoxyborohydride, sodium borohydride, sodium cyanoborohydride, and so forth. Exemplary borane reducing agents include borane dimethyl sulfide complex, 9-borabicyclo[3.3.1]nonane, borane 1,2-bis(t-butylthio)ethane complex, borane t-butylamine complex, borane di(t-butyl)phosphine complex, borane-tetrahydrofuran complex, and so forth. In one particular embodiment, the reducing agent is sodium triacetoxyborohydride.

Formation of compound 7 is typically conducted at a temperature ranging from about −5° C. to about 10° C.; and in one embodiment at a temperature of about 0° C. The reaction is typically allowed to progress for about 5 to about 60 minutes, and in one embodiment for about 10 to about 20 minutes.

The second step is the debenzylation of compound 7 to yield compound 8. Typically, debenzylation can be done using hydrogen or ammonium formate, in the presence of a catalyst, such as a palladium catalyst. Representative catalysts include, by way of illustration, palladium on carbon, palladium hydroxide on carbon and the like. This reaction is typically conducted at a temperature ranging from about 20-40° C., typically about 25° C., for about 2-6 hours or until the reaction is substantially complete. Generally, this reaction is conducted in an inert, such as methanol, ethanol, isopropanol, methyltetrahydrofuran, and the like. Upon completion of the reaction, compound 8 is typically isolated using conventional procedures, such as extraction, recrystallization, chromatography and the like. In one embodiment, the compound of formula 8 is isolated by recrystallization using methyl t-butyl ether and isopropanol.

Compound of Formula 3

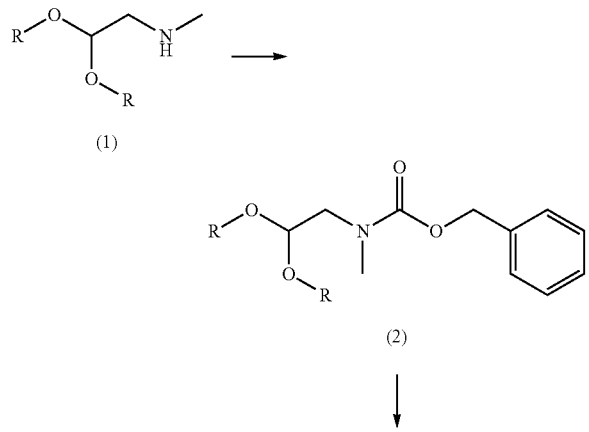

The compound of formula 3 is prepared by the carbobenzyloxy protection of compound 1, where each R is independently $C_{1-6}$alkyl or are taken together to form a dioxane or dioxolane, to yield compound 2, followed by acetal deprotection of compound 2. Compound 1 is either commercially available or is readily synthesized by techniques that are well known in the art. Exemplary $C_{1-6}$alkyl groups include methyl and ethyl, and exemplary dioxane and dioxolane groups include 1,3-dioxane and 1,3-dioxolane.

Typically, the acetal compound 1 is dissolved in an inert diluent, then added to a base. In one embodiment, one equivalent of compound 1 is combined with one or more equivalents of the base. Protection of the acetal is then done by the addition of benzyl chloroformate. Generally an excess of compound 1 is used based on the amount of benzyl chloroformate, typically from about 1 to about 2 equivalents of the acetal compound 1 are used, and in another embodiment, about 1.7 to about 1.8 equivalents are used. In one embodiment, the base is an alkali metal carbonate, and in one particular embodiment, potassium carbonate.

Typically, this process is conducted in a single reaction vessel without isolation of intermediate reaction products. Generally, for a multi-step process that is conducted in a single reaction vessel, the inert diluent is selected so as to be compatible with the materials used in each step. In one embodiment, the inert diluent is the same in each of the two steps used for preparing compound 3; and in a particular embodiment, the inert diluent is methyltetrahydrofuran.

Then acetal-base mixture is typically maintained at a cooled temperature since the addition of benzyl chloroformate is exothermic. In one embodiment the acetal-base mixture is maintained at a temperature ranging from about 0° C. to about 10° C.; and in one embodiment at a temperature ranging from about 0° C. to about 5° C. After addition of the benzyl chloroformate, the reaction mixture is typically maintained at about room temperature.

Compound 1 and compound 2 have an acetal protecting group, which is depicted as "R", which is a group covalently attached to the acetal that prevents it from undergoing undesired reactions but which permits the acetal to be converted to the aldehyde upon treatment of the protecting group with a suitable reagent. Representative acetal protecting groups include, but are not limited to, $C_{1-6}$alkyl, dioxane, dioxolane, and the like. In one particular embodiment, the acetal protecting group is methyl. Other representative acetal protecting groups are described, for example, in T. W. Greene and G. M. Wuts, *Protecting Groups in Organic Synthesis*, Third Edition, Wiley, New York, 1999.

The second step of the process is an acetal deprotection step, which involves removing the acetal protecting group, R, from compound 2 to provide the aldehyde compound 3. Standard deprotection techniques and reagents such as HCl and TFA are used to convert the acetal to the aldehyde. See also, T. W. Greene, supra. Protection of the readily available compound, followed by deprotection under acidic condition is also described in Martin et al. (1987 *J. Org. Chem.* 52:1962-1972.

Typically, compound 2 and the deprotecting reagent are combined in an inert diluent. This deprotection step is typically conducted at a temperature ranging from about 10° C. to about 30° C.; and in one embodiment at a temperature ranging from about 15° C. to about 25° C. for about 20 to about 28 hours, and in one embodiment for about 18 hours, or until the reaction is substantially complete. In one embodiment, the deprotecting reagent is HCl such as 3N HCl, and the inert diluent is methyltetrahydrofuran.

In one embodiment, compound 3 can be used directly in the synthesis of compound 8 without being isolated.

Compound of Formula 6

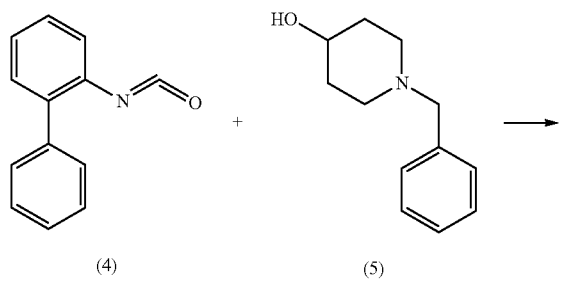

(4)          (5)

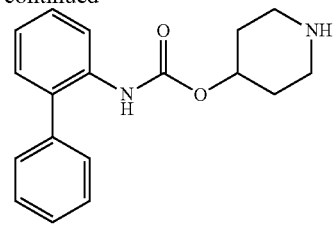

(6)

The carbamate compound of formula 6 is prepared by treating the isocyanate compound 4 with the phenol compound 5, followed by removal of the amino-protecting group. Approximately equimolar amounts of the isocyanate and phenol compounds are combined in an N-hydro-C-alkoxy addition reaction to form the carbamate. The benzyl protecting group can be removed by reduction, for example, by reaction with ammonium formate and a Group VIII metal catalyst, such as palladium.

Crystalline Freebase of the Compound of Formula I
(Form III)

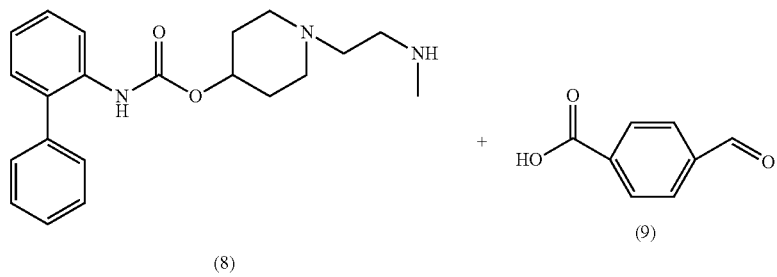

(8)          (9)

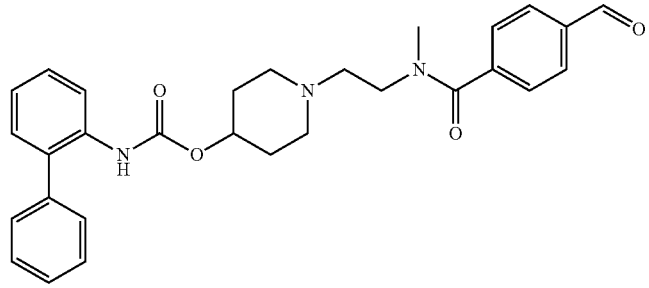

(10)

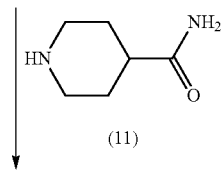

(11)

-continued

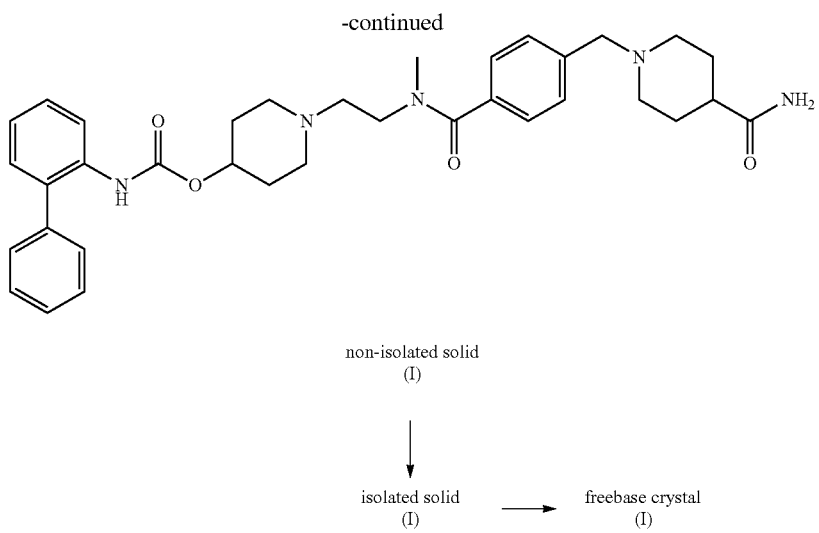

non-isolated solid
(I)

↓ isolated solid          →          freebase crystal
(I)                                        (I)

The process for preparing the compound of formula I is conducted in four steps, and the first two steps are conducted in a single reaction vessel without isolation of intermediate reaction products. Generally, for a multi-step process that is conducted in a single reaction vessel, the inert diluent is selected so as to be compatible with the materials used in each step. In one embodiment, the inert diluent is the same in each of the first three steps used for preparing the compound of formula I; and in a particular embodiment, the inert diluent is methyltetrahydrofuran.

The first step of the process is a coupling reaction that forms compound 10. This step involves combining about one equivalent of the amine compound 8 with one or more equivalents of the carboxylic acid compound 9, in the presence of one or more equivalents of an amine-carboxylic acid coupling reagent to form compound 10. Compound 9 is commercially available and can also be prepared by conventional procedures using commercially available starting materials and conventional reagents.

Typically, the amine and the carboxylic acid are combined in an inert diluent in the presence of a coupling reagent to form a reaction mixture. In one embodiment, from about 1 to about 2 equivalents of the carboxylic acid are used based on the amount of amine; and in another embodiment, about 1.0 equivalents are used. In one embodiment, from about 1 to about 2 equivalents of the coupling reagent are used based on the amount of amine; and in another embodiment, about 1.1 equivalents are used.

Suitable amine-carboxylic acid coupling reagents include: 4-(4,6-dimethoxy-1,3,5-triazin-2-yl)-4-methylmorpholinium chloride (DMTMM Cl), tetrafluoroborate (DMTMM $BF_4$) and hexafluorophosphate (DMTMM $PF_6$); (2-(6-chloro-1H-benzotriazole-1-yl)-1,1,3,3-tetramethylaminium hexafluorophosphate (HCTU), benzotriazol-1-yloxytris(dimethylamino)phosphonium hexafluorophosphate (BOP), benzotriazol-1-yloxytripyrrolidinophosphonium hexafluorophosphate (PyBOP), and O-(7-azabenzotriazol-1-yl-N,N,N',N'-tetramethyluronium hexafluorophosphate (HATU); dicyclohexylcarbodiimide (DCC), N-(3-dimethylaminopropyl)-N'-ethylcarbodiimide (EDC), and carbonyldiimidazole (CDI); and the like. In one embodiment, the coupling reagent is a 4-(4,6-dimethoxy-1,3,5-triazin-2-yl)-4-methylmorpholinium compound, in particular DMTMM Cl.

The coupling reaction is typically conducted at room temperature; and in one embodiment at room temperature for about 8 to about 24 hours, or until formation of compound 10 is substantially complete. When formation of compound 10 is substantially complete, any solids can be filtered off and the filtrate can be further treated prior to use in the next step. Such treatment may include washing the filtrate with a $NaHCO_3$ solution, separating the layers, washing the organic layer with a NaCl solution, separated the layers, and discarding the aqueous layer. The resulting solution may also be concentrated (e.g., under reduced pressure and at room temperature), prior to use in the next step.

The second step of the process is a reductive amination reaction that forms the compound of formula I (non-isolated form). This step involves combining about one equivalent of compound 10 with one or more equivalents of compound 11 and one or more equivalents of a reducing agent. Compound 11 is commercially available and can also be prepared by conventional procedures using commercially available starting materials and conventional reagents.

This reductive amination step is conducted at an elevated temperature and azeotropic distillation of water is conducted prior to the addition of the reducing agent. Typically, the elevated temperature is within the range of about 40-70° C., and in one embodiment is within the range of about 55-65° C. The azeotropic distillation is generally conducted with a low molecular weight alcohol such as methanol, ethanol or isopropanol. Use of azeotropic distillation avoids aldehyde reduction as a side reaction as well as minimizing by-product formation.

Typically, the reducing agent is added to a mixture of compound 10 and compound 11 in an inert diluent such as isopropanol. In one embodiment, about 2.0 to 4.0 equivalents of the reducing agent are used and about 1.0 to 3.0 equivalents of compound 11 are used, based on the amount of compound 10; and in another embodiment, about 3.0 equivalents of the reducing agent and about 2.0 equivalents of compound 11 are used based upon 1.0 equivalents of compound 10. Suitable reducing agents include metal hydride reagents and borane reducing agents, as described herein. In one particular embodiment, the reducing agent is sodium triacetoxyborohydride. The reductive amination step is typically conducted at a temperature ranging from about 0° C. to about 65° C.; and in one embodiment at an initial elevated temperature ranging from about 55° C. to about 65° C., followed by cooling to about room temperature, the further cooling to a temperature ranging from about 15° C. to about 20° C. during addition of the reducing agent, and finally allowing the reaction mixture to warm to room temperature.

The third step of the process involves contacting the compound of formula I (non-isolated form) with isopropyl acetate, and in one embodiment, followed by seeding with crystalline freebase (Form III). Typically, the seed crystal can be prepared as described in U.S. Patent Application Publication No. 2011/0015163 to Woollham. In one embodiment, the seed crystal is micronized. This step is typically initially conducted at about room temperature. After a slurry is formed, the temperature may be lowered to facilitate precipitation, generally cooling to a temperature ranging from about 0° C. to about 10° C. The solids are then filtered (the compound of formula I, isolated solids) and used in the next step, generally after being washed with isopropyl acetate and dried.

The fourth step of the process involves contacting the compound of formula I (isolated solids) with toluene, and in one embodiment, followed by seeding with crystalline freebase (Form III). In one embodiment, the seed crystal is micronized. This step is typically initially conducted at an elevated temperature, for example, at a temperature ranging from about 75° C. to about 90° C. The temperature may then be lowered to facilitate precipitation, generally initially cooling to a temperature ranging from about 45° C. to about 65° C., then cooling to about room temperature. The solid product is then filtered and dried.

As is well known in the field of powder x-ray diffraction, relative peak heights of powder x-ray diffraction (PXRD) spectra are dependent on a number of factors relating to sample preparation and instrument geometry, while peak positions are relatively insensitive to experimental details. The PXRD pattern for the solid product was evaluated and was determined to be the crystalline freebase Form III, based upon comparison with the PXRD for the crystalline freebase Form III described in U.S. Patent Application Publication No. 2011/0015163 to Woollham.

Further details regarding specific reaction conditions and other procedures for preparing representative compounds of the invention or intermediates thereof are described in the Examples set forth below.

EXAMPLES

The following Preparations and Examples are provided to illustrate specific embodiments of the invention. These specific embodiments, however, are not intended to limit the scope of the invention in any way unless specifically indicated. The following abbreviations have the following meanings unless otherwise indicated and any other abbreviations used herein and not defined have their standard meaning:

| | |
|---|---|
| AcOH | acetic acid |
| EtOAc | ethyl acetate |
| EtOH | ethanol |
| IPA | isopropanol |
| iPrOAc | isopropyl acetate |
| MeCN | acetonitrile |
| MeOH | methanol |
| MTBE | methyl t-butyl ether |
| MeTHF | 2-methyltetrahydrofuran |
| NaHB(OAc)$_3$ | sodium triacetoxyborohydride |

Any other abbreviations used herein but not defined have their standard, generally accepted meaning. Unless noted otherwise, reagents, starting materials and solvents were purchased from commercial suppliers (such as Sigma-Aldrich, Fluka, and the like) and were used without further purification.

Preparation 1

Biphenyl-2-yl-carbamic acid piperidin-4-yl Ester

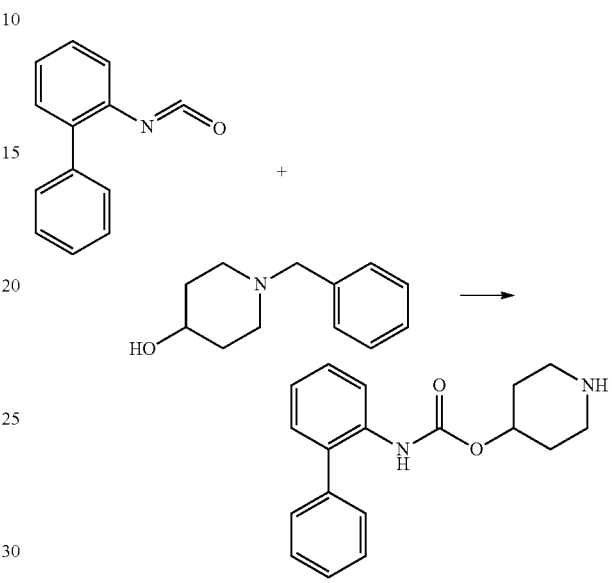

Biphenyl-2-isocyanate (97.5 g, 521 mmol) and 1-benzylpiperidin-4-ol (105 g, 549 mmol) were heated together at 70° C. for 12 hours. The mixture was then cooled to 50° C. and EtOH (1 L) was added, followed by the slow addition of 6M HCl (191 mL). The resulting mixture was then cooled to ambient temperature. Ammonium formate (98.5 g, 1.6 mol) was added and then nitrogen gas was bubbled through the solution vigorously for 20 minutes. Palladium on activated carbon (20 g, 10 wt % dry basis) was added and the mixture was heated at 40° C. for 12 hours, and then filtered. The solvent was removed under reduced pressure and 1M HCl (40 mL) was added to the crude residue. The pH of the mixture was adjusted with 10 N NaOH to pH 12. The aqueous layer was extracted with EtOAc (2×150 mL), and the organic layer was dried over MgSO$_4$, filtered and the solvent removed under reduced pressure to yield the title compound (155 g). HPLC (10-70) R$_f$=2.52; m/z: [M+H$^+$] calcd for C$_{18}$H$_{20}$N$_2$O$_2$ 297.15; found 297.3.

Example 1

Step A: (2,2-Dimethoxyethyl)methylcarbamic Acid Benzyl Ester

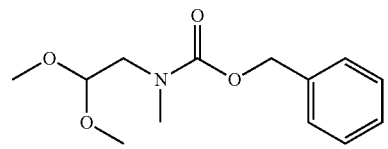 [SMILES: COC(CN(C)C(=O)OCc1ccccc1)OC]

K$_2$CO$_3$ (13.8 g, 100 mmol, 1.76 eq.) and H$_2$O (46 mL) were mixed to form a homogeneous solution. The solution was cooled to 20° C. N-methylaminoacetaldehyde dimethylacetal (12.8 mL, 100 mmol, 1.8 eq) and MeTHF (50 mL) were added. The resulting mixture was cooled to 2° C. Benzyl chloroformate (8.1 mL, 56.7 mmol, 1.0 eq.) was added by syringe over 10 minutes (addition was exothermic). The mixture was maintained at room temperature until completion of the reaction. The layers were separated and the organic layer was washed with 1N HCl (50 mL) and used directly in the next step.

Step B: Methyl-(2-oxoethyl)carbamic Acid Benzyl Ester

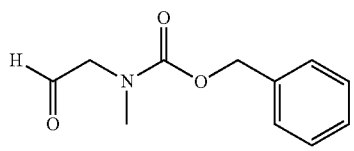

The mixture from the previous step was combined with a 3N HCl solution (70 mL), and the resulting mixture was stirred for 18 hours at 22° C. to yield a clear homogeneous pale yellow solution. Solid NaHCO₃ was added to the solution to bring the pH to neutral. The layers were separated and the aqueous layer was back-extracted with MeTHF (20 mL). The organic layers were combined and washed with a saturated NaHCO₃ solution (50 mL). The layers were separated and the organic layer was dried over Na₂SO₄, filtered and concentrated to dryness to afford the title compound (11.9 g) as a pale yellow oil.

Step C: Biphenyl-2-yl-carbamic acid 1-[2-(benzyloxycarbonyl methylamino)ethyl]piperidin-4-yl Ester

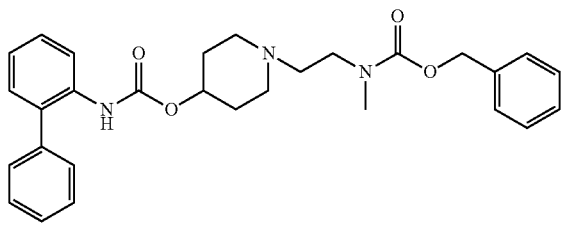 [SMILES: CN(CCN1CCC(OC(=O)Nc2ccccc2-c2ccccc2)CC1)C(=O)OCc1ccccc1]

Biphenyl-2-yl-carbamic acid piperidin-4-yl ester (31.1 g, 105 mmol, 1.0 eq.) and MeTHF (150 mL) were mixed. A solution of methyl-(2-oxoethyl)carbamic acid benzyl ester (23 g, 113.4 mmol, 1.05 eq.) in MeTHF (150 mL) was prepared and added to the ester mixture. The resulting mixture was heated to 30° C. for a few minutes, then cooled to room temperature over 1 hour. The mixture was then cooled to 3° C. and the temperature maintained for 1 hour. NaHB(OAc)₃ (35.1 g, 170 mmol, 2.0 eq.) was added portion-wise while maintaining the internal temperature at 7±1° C. After addition, the mixture was allowed to warm to room temperature until the reaction was complete. A saturated solution of NaHCO₃ (3000 mL) was added, stirred for 20 minutes, and the layers separated. This was repeated, after which the organic layer was dried over Na₂SO₄. The material was filtered, concentrated and dried under high vacuum to afford the title compound (43 g) as a thick colorless to pale yellow oil, which was used directly in the next step without purification.

Step D: Biphenyl-2-yl-carbamic acid 1-(2-methylaminoethyl)piperidin-4-yl Ester

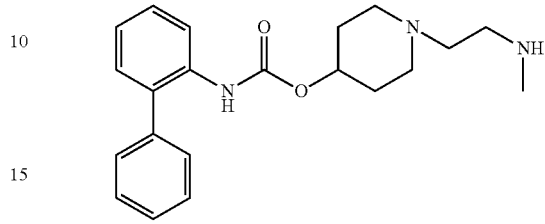

Biphenyl-2-yl-carbamic acid 1-[2-(benzyloxycarbonyl methylamino)ethyl]piperidin-4-yl ester (53 g, 105 mmol, 1 eq.), MeOH (250 mL), and MeTHF (50 mL) were combined under nitrogen. 10% palladium on carbon (0.8 g) was added and hydrogen was bubbled into the mixture for 1 minute. The reaction vessel was sealed and stirred under hydrogen at atmospheric pressure for three hours. The mixture was then filtered, and the solids were washed MeTHF (10 mL).

The filtrate and washes were combined and concentrated under reduced pressure (250 mL removed). MTBE (100 mL) was added, and the solution again concentrated under reduced pressure (100 mL removed). MTBE (200 mL) was added and the solution was seeded with a few milligrams of biphenyl-2-yl-carbamic acid 1-(2-methylaminoethyl) piperidin-4-yl ester, and the mixture was maintained for 3 hours. The solids were collected and the vessel and filter cake were washed with MTBE (2×15 mL). The material was dried to yield 13.2 g of the title compound (99.5% pure). This process was repeated to yield the title compound (12.5 g, 98.6% pure). The filtrate and washes were combined and concentrated under reduced pressure. MTBE (150 mL) was added and the solution was seeded with a few milligrams of biphenyl-2-yl-carbamic acid 1-(2-methylaminoethyl) piperidin-4-yl ester, and the mixture was maintained for 20 hours. The solids were collected and the vessel and filter cake were washed with MTBE (2×15 mL). The material was dried to yield the title compound (5 g, 90% pure).

A portion of the three crops (13 g, 12 g, 4.5 g, respectively) were combined taken up in IPA (90 mL). The resulting slurry was heated to 45° C., then cooled to room temperature over 1 hour. The slurry was stirred for 5 hours at 25° C. The solids were collected and washed with IPA (2×15 mL). The solids were then dried for 1 hour to yield the title compound (25 g, >99% pure).

Example 2

All volumes and molar equivalents are given relative to biphenyl-2-yl-carbamic acid piperidin-4-yl ester.

Step A: (2,2-Dimethoxyethyl)methylcarbamic Acid Benzyl Ester

K₂CO₃ (8.4 kg, 60 mol, 1.8 eq.) and H₂O (49.3 kg, 2.6 volumes) were placed in the reaction vessel and stirred. N-methylaminoacetaldehyde dimethylacetal (6.5 kg, 54 mol, 1.6 eq) and MeTHF (20.2 kg, 2.9 volumes) were added. The resulting mixture was cooled to 5° C. Benzyl chloroformate (6.8 kg, 37.6 mol, 1.1 eq.) was added over a period of about 30 minutes, while maintaining the temperature below 10° C. The feed line was rinsed with MeTHF (4.3 kg). The mixture was then maintained at 5° C. and stirred for 1 hour. The layers were separated and the organic layer was washed with 1N HCl (14.3 kg, 11.7 mol, 1.4 volumes) and used directly in the next step.

Step B: Methyl-(2-oxoethyl)carbamic Acid Benzyl Ester

The mixture from the previous step was combined with water (23.4 kg, 2.9 volumes) and 30% hydrochloric acid (13.1 kg, 107.7 mol, 1.1 volumes). Water (5.1 kg) was used to rinse the feed line. The temperature was adjusted to 25-30° C., and the reaction was run for 16-24 hours. A 25% NaOH solution (11.8 kg, 71.1 mol, 2.2 eq.) was added to the solution to adjust the pH and obtain phase separation.

The layers were separated and the aqueous layer was back-extracted with MeTHF (10.0 kg, 1.1 volumes). The aqueous layer was discarded and the organic layers were combined. MeTHF (4.4 kg) was used to rinse the feed line. The organics were washed with a saturated NaHCO$_3$ solution (14.6 kg, 15.6 mol, 1.1 volumes). The layers were separated and the organic layer was dried over Na$_2$SO$_4$ (2.5 kg, 17.6 mol) for 60-90 minutes. The drying agent was filtered off and the remaining solids were washed with MeTHF (8.8 kg, 1 volume). The reaction vessel was washed with water and MeOH before continuing with the next step.

Step C: Biphenyl-2-yl-carbamic acid 1-[2-(benzyloxycarbonyl methylamino)ethyl]piperidin-4-yl Ester The product from the previous step (in MeTHF) and biphenyl-2-yl-carbamic acid piperidin-4-yl ester (10.0 kg, 32.6 mol, 1.0 eq.) in MeTHF (28.5 kg) were placed in the reaction vessel and heated to 30° C. for one hour. The mixture was then cooled to 5° C. NaHB(OAc)$_3$ (10.0 kg, 45.8 mol, 1.4 eq.) was added portion wise over a period of 40 minutes while maintaining the temperature below 20° C. The mixture was then stirred for 30 minutes. Additional NaHB(OAc)$_3$ (0.5 kg) was added the reaction allowed to progress to completion. A saturated solution of NaHCO$_3$ (14.3 kg, 15.3 mol, 1.1 volumes) was added and stirred for 10 minutes. The aqueous phase was separated and discarded. A 33% NaOH solution (15.8 kg, 129.9 mol, 4.0 eq.) was added to the reaction mixture to adjust the pH to be in the range of 8-12. Water (40 kg) was added in two portions, after which phase separation occurred. A saturated NaHCO$_3$ (7.1 kg, 7.6 mol, 0.7 volumes) was added to the reaction mixture and stirred for 10 minutes. The aqueous phase was separated and discarded. Additional water (4.9 kg) was added to dissolve any remaining salts and a vacuum distillation was conducted at a maximum temperature of 45° C. to remove part of the solvent (7.2 volumes). MeOH (56.1 kg, 7.2 volumes) was added to the reaction mixture before continuing with the next step.

Step D: Biphenyl-2-yl-carbamic acid 1-(2-methylaminoethyl)piperidin-4-yl Ester 10% palladium on carbon (0.4 kg, 0.03 wt %, Degussa type 101 NE/W) was added to the reaction mixture. A hydrogenation reaction was performed to remove the benzyloxycarbonyl protective group, with reaction conditions at 30±5° C. and 4 bar pressure. The reaction was run until completion. The mixture was then filtered and the filter cake was washed with MeOH (8.0 kg, 1.0 volume). The reaction was continued in a clean vessel, which was charged with the product solution (in MeTHF/MeOH) from the hydrogenation reaction. 3-Mercaptopropyl silica (0.6 kg, 0.07 wt %, Silicycle) was added. MeOH (4.8 kg) was used to rinse the feed line. The reaction mixture was stirred for 14-72 hours at 25±5° C. Activated carbon (0.7 kg, 0.07 wt %) was added and the mixture stirred for 30 minutes. The mixture was filtered and the filter cake was washed with MeOH (1.0 volume). The reaction was continued in a clean vessel, which was charged with the product solution (in MeTHF/MeOH), and MeOH (4.2 kg) was used to rinse the feed line. The mixture was heated to 40-45° C. and a vacuum distillation was performed to bring the final volume to 5.6 volumes (removal of methanol).

2-propanol (40.2 kg, 5.0 volumes) was added and distillation continued until the volume was reduced to 2.5 volumes. The solids were then isolated by filtration and washed with MTBE (1.5 volumes) to yield the product as a wet cake (8.6 kg, 96.8% purity). The cake was charged to the reaction vessel and additional 2-propanol (1.9 volumes) was added. The mixture was warmed to 40±5° C., and maintained at that temperature for 2 hours. The mixture was then slowly cooled over a minimum of 4 hours to 20° C., then actively cooled to 5-10° C., followed by stirring for 2 hours. The product was filtered and the resulting cake washed with MTBE (1.0 volume). The solids were then dried under atmospheric conditions to yield the title compound (6.6 kg, 98.5% purity).

Example 3

Crystalline Freebase of Biphenyl-2-yl-carbamic Acid 1-{2-[(4-carbamoylbenzoyl) methylamino] ethyl}piperidin-4-yl Ester (Form III)

Step A: Biphenyl-2-yl-carbamic acid 1-{2-[(4-formylbenzoyl)methylamino]ethyl}piperidin-4-yl Ester

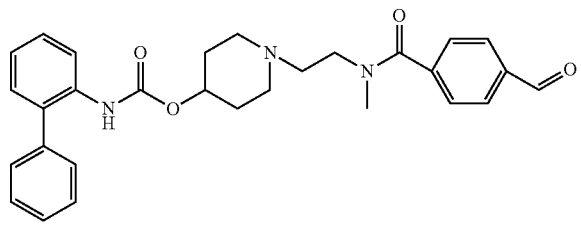 [SMILES: CN(CCN1CCC(OC(=O)Nc2ccccc2-c2ccccc2)CC1)C(=O)c1ccc(C=O)cc1]

4-Carboxybenzaldehyde (9 g, 60 mmol, 1.0 eq.) and biphenyl-2-yl-carbamic acid 1-(2-methylaminoethyl)piperidin-4-yl ester (21.2 g, 60 mmol, 1.0 eq.) were combined in MeTHF (115 mL). The mixture was stirred for 0.5 hours, forming a thick slurry. Additional MeTHF (50 mL) was added to form a free-flowing slurry. 4-(4,6-dimethoxy-1,3,5-triazin-2-yl)-4-methylmorpholinium chloride (18 g, 63 mmol, 1.1 eq., 97% pure) was added in two portions and the funnel rinsed with additional MeTHF (50 mL). The mixture was stirred at room temperature overnight. MeCN (50 mL) was added and the mixture was filtered. The solids were washed with MeTHF (30 mL). The filtrate and washes were combined and a saturated NaHCO$_3$ solution (100 mL) was added and stirred for 10 minutes. The layers were separated and a saturated NaCl solution (100 mL) was added and stirred for 10 minutes. The layers were separated and the aqueous layer discarded. The resulting solution was concentrated under reduced pressure and held at room temperature for three days, then used directly in the next step.

Step B: Biphenyl-2-yl-carbamic acid 1-{2-[(4-carbamoylbenzoyl)methylamino]ethyl}piperidin-4-yl ester (Non-Isolated Form)

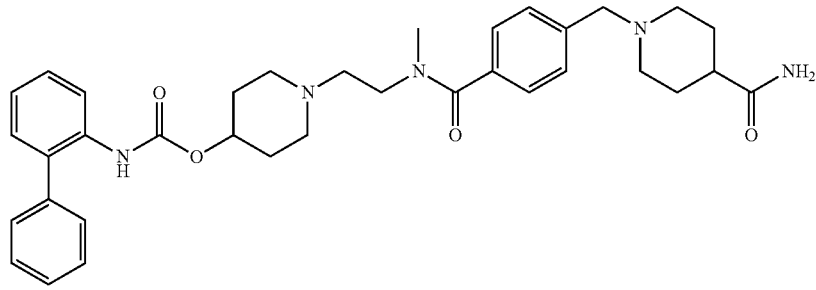 [SMILES: CN(CCN1CCC(OC(=O)Nc2ccccc2-c2ccccc2)CC1)C(=O)c1ccc(CN2CCC(C(N)=O)CC2)cc1]

Isonipecotamide (15.4, 120 mmol, 2.0 eq.) and IPA (200 mL) were added to the solution of biphenyl-2-yl-carbamic acid 1-{2-[(4-formylbenzoyl)methylamino]ethyl}piperidin-4-yl ester from the previous step. Liquid (200 mL) was distilled off and additional IPA (400 mL) was added under reduced pressure at 60° C. Liquid (400 mL) was distilled off over a period of 1.5 hours and additional IPA (600 mL) was added. Liquid (100 mL) was distilled off and the remaining solution was cooled to 30° C. to yield a hazy white mixture, which was then added to $Na_2SO_4$ (18 g). The flask was rinsed with IPA (100 mL) and added to the solution. The resulting mixture was cooled to room temperature and AcOH (20 mL, 360 mmol, 6.0 eq.) was added. The mixture was cooled to 18° C. with an ice bath and $NaHB(OAc)_3$ (38.2 g, 180 mmol, 3.0 eq.) was added over 5 minutes. The mixture was allowed to warm up to 25° C. and was maintained at that temperature for 2 hours. Solvent was removed under reduced pressure, and the remaining material was used directly in the next step.

Step C: Biphenyl-2-yl-carbamic acid 1-{2-[(4-carbamoylbenzoyl) methylamino]ethyl}piperidin-4-yl ester (Isolated Solid)

iPrOAc (300 mL) was added to the material, followed by the addition of water (200 mL). The pH of the solution was adjusted to pH 1 with 3N HCl (~150 mL). The layers were separated and the organic layer was discarded. The aqueous layer was collected, and iPrOAc (300 mL) was added. The pH of the solution was adjusted to basic pH with 50 wt % NaOH (~100 mL). The resulting mixture was stirred for 15 minutes and the layers were separated. The organic layer was filtered and seeded with micronized crystalline freebase of biphenyl-2-yl-carbamic acid 1-{2-[(4-carbamoylbenzoyl)methylamino]ethyl}piperidin-4-yl ester (Form III; prepared as described in U.S. Patent Application Publication No. 2011/0015163 to Woollham) and stirred overnight at room temperature to yield a white slurry. Stirring was continued for 8 hours at room temperature and for 16 hours at 5° C. (cold room). The mixture was slowly filtered under pressure. The cake was washed with cold iPrOAc (2×20 mL) and dried under nitrogen to yield a white solid (27.5 g). The material was further dried in a vacuum oven at 30° C. for 24 hours to yield 25.9 g.

Step D: Crystalline Freebase of Biphenyl-2-yl-carbamic Acid 1-{2-[(4-carbamoylbenzoyl)methylamino]ethyl}piperidin-4-yl Ester (Form III)

The white solid (5 g, 60 mmol, 1.0 eq.) was dissolved in toluene (75 mL) and the resulting mixture was heated to 82° C. to yield a clear solution. The solution was filtered. The solids were washed with toluene (2×5 mL), and the filtrate and washes were combined. The mixture was cooled to 60° C. and seeded with micronized crystalline freebase of biphenyl-2-yl-carbamic acid 1-{2[(4-carbamoylbenzoyl)methylamino]ethyl}piperidin-4-yl ester (Form III; prepared as described in Example 3 in U.S. Patent Application Publication No. 2011/0015163 to Woollham). The mixture was maintained at 55° C. for 2 hours, then cooled to room temperature on an oil bath overnight (~16 hours). The resulting slurry was then filtered and the cake was dried for 3 hours to yield a solid while material (4.6 g). The material was further dried in a vacuum oven at 30° C. for 24 hours (exhibited no further weight loss) to yield the title compound (4.6 g).

The product was analyzed by powder x-ray diffraction, differential scanning calorimetry and thermal gravimetric analysis, and was determined to be the crystalline freebase (Form III) of biphenyl-2-ylcarbamic acid 1-(2-{[4-(4-carbamoylpiperidin-1-ylmethyl)benzoyl]methylamino}ethyl) piperidin-4-yl ester described in U.S. Patent Application Publication No. 2011/0015163 to Woollham.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:
1. A process for preparing a compound of formula 8:

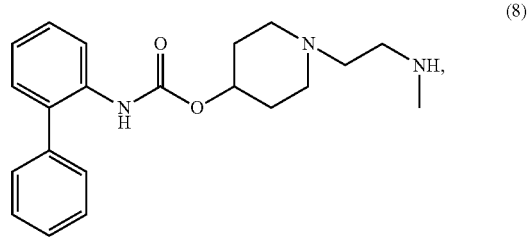 [SMILES: CNCCN1CCC(OC(=O)Nc2ccccc2-c2ccccc2)CC1]

the process comprising the steps of:
(a) reductive amination of a compound of formula 3:

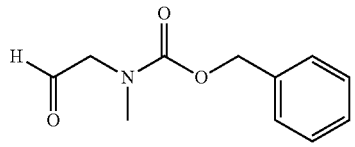
(3)

and a compound of formula 6:

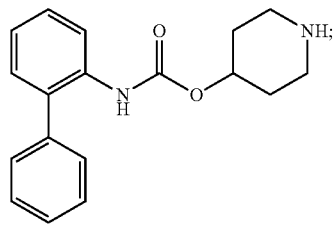
(6)

in the presence of a reducing agent, to yield the compound of formula 7:

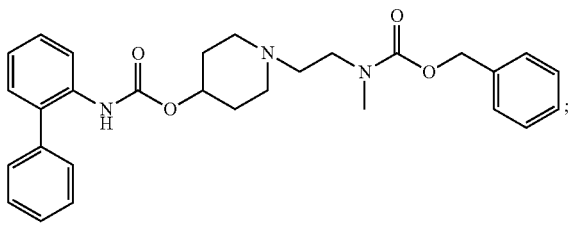
(7)

and
(b) debenzylation of the compound of formula 7 to yield the compound of formula 8; wherein step (a) and step (b) are conducted in the same reaction mixture without isolation of the intermediate from step (a); wherein steps (a) and (b) are conducted in methyltetrahydrofuran.

2. The process of claim 1, wherein the reducing agent in step (a) is sodium triacetoxyborohydride.

3. The process of claim 1, wherein the compound of formula 3 is prepared by the process comprising the steps of:
(i) carbobenzyloxy protection of a compound of formula 1:

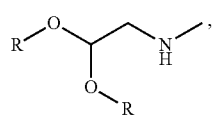
(1)

where each R is independently $C_{1-6}$alkyl or are taken together to form a dioxane or dioxolane, to yield the compound of formula 2:

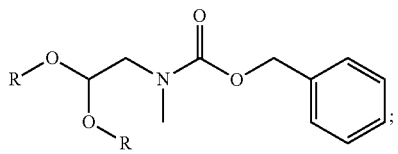
(2)

and
(ii) acetal deprotection of the compound of formula 2 to yield the compound of formula 3; wherein steps (i) and (ii) are conducted in methyltetrahydrofuran, and wherein step (ii) and step (a) are conducted in the same reaction mixture without isolation of the intermediate from step (ii).

4. The process of claim 3, wherein step (i) comprises combining the compound of formula 1 and benzyl chloroformate.

* * * * *